(12) United States Patent
Rice et al.

(10) Patent No.: US 6,537,207 B1
(45) Date of Patent: Mar. 25, 2003

(54) IDENTIFICATION OF PROTECTIVE COVERS FOR MEDICAL IMAGING DEVICES

(75) Inventors: Mark J. Rice, Johnson City, TN (US); Steve Spanoudis, Coral Springs, FL (US)

(73) Assignee: Fovioptics, Inc., Lexington, KY (US)

( * ) Notice: Subject to any disclaimer, the term of this patent is extended or adjusted under 35 U.S.C. 154(b) by 0 days.

(21) Appl. No.: 09/958,280

(22) PCT Filed: Apr. 6, 2000

(86) PCT No.: PCT/US00/09431
§ 371 (c)(1),
(2), (4) Date: Oct. 5, 2001

(87) PCT Pub. No.: WO00/59366
PCT Pub. Date: Oct. 12, 2000

Related U.S. Application Data
(60) Provisional application No. 60/128,151, filed on Apr. 7, 1999.

(51) Int. Cl.[7] ............................................... A61B 1/00
(52) U.S. Cl. ...................................... 600/121; 600/103
(58) Field of Search ............................... 600/121, 122, 600/133, 103, 176, 175, 117, 118

(56) References Cited
U.S. PATENT DOCUMENTS

| | | | |
|---|---|---|---|
| 4,603,976 A | 8/1986 | Fetzer et al. | 356/402 |
| 4,757,381 A | 7/1988 | Cooper et al. | 358/98 |
| 4,809,342 A | 2/1989 | Kappner et al. | 382/11 |
| 5,168,863 A | 12/1992 | Kurtzer | 128/4 |
| 5,201,908 A | 4/1993 | Jones | 128/4 |
| 5,359,991 A | 11/1994 | Takahashi et al. | 128/4 |
| 5,363,838 A | 11/1994 | George | 128/6 |
| 5,363,843 A | 11/1994 | Daneshvar | 128/630 |
| 5,406,939 A | 4/1995 | Bala | 128/4 |
| 5,627,895 A | 5/1997 | Owaki | 380/54 |
| 5,743,849 A | 4/1998 | Rice et al. | 600/186 |
| 5,820,547 A | * 10/1998 | Strobl et al. | 600/127 |

\* cited by examiner

*Primary Examiner*—John P. Leubecker
(74) *Attorney, Agent, or Firm*—Foley & Lardner

(57) ABSTRACT

A protective cover for medical imaging devices of the type having a probe with an optical system at a distal end includes a sheath of plastic material formed to enclose at least a portion of the probe and a transparent head secured to the sheath at a distal end of the cover. The transparent head provides a transparent window at the distal end of the probe to allow light to enter the probe and be imaged in a normal manner. Indicia are formed on the transparent head and are imaged by the medical imaging device. The image is then analyzed to determine if the indicia as shown in the image correspond to a preselected pattern, which may be one of a group of patterns which provide indications concerning the nature of the cover. If a pattern is recognized, the information corresponding to that pattern can be provided to an operator; if no pattern is recognized or if the pattern corresponds to an improper cover for the particular imaging device, a warning can be provided to the operator or the device disabled. The protective cover can be disposed after use with a patient, and a new cover applied to enclose the portions of the probe that will contact another patient, thereby minimizing potential spread of infection.

30 Claims, 4 Drawing Sheets

IDENTIFICATION OF PROTECTIVE COVERS FOR MEDICAL IMAGING DEVICES

This application claims the benefit of No. 60/128,151, filed Apr. 7, 1999.

FIELD OF THE INVENTION

The present invention relates generally to medical imaging devices and more particularly to protective covers for providing infection control barriers for such devices.

BACKGROUND OF THE INVENTION

Each time a medical instrument or device comes in direct contact with a patient there is a danger of cross-contamination between patients, from patients to medical personnel, or vice versa. Therefore, medical devices and instruments that come in direct contact with patients are thoroughly cleaned between uses. For many large, expensive, or complicated medical devices, which are difficult or impossible to clean using conventional methods, cross-contamination prevention is provided by the use of a protective cover placed over the device or over a portion of the device which will come in direct contact with a patient. A clean protective cover is placed on the medical device before each use. Although such protective covers may be cleaned and re-used, typically such protective covers are intended for only a single use and are disposable. Disposable protective covers for medical instruments or devices are typically made of a flexible or semi-rigid plastic material which is generally shaped to fit over the medical instrument or device with which the cover is designed to be used. Examples of medical devices for which such disposable protective covers are regularly employed include laryngoscopes, endoscopes, ultrasound probes, and transesophageal echocardiographic probes. One such device is shown in U.S. Pat. No. 5,363,838. Examples of disposable covers for medical devices are shown in U.S. Pat. Nos. 4,757,381, 5,168,863, 5,201,908, 5,359,991, 5,363,843, 5,406,939, and 5,743,849.

In recent years, advancements in video imaging technology have enabled the development of video imaging medical devices and video imaging accessories for existing medical devices. Examples of such medical imaging devices include dental cameras, retinal cameras, laryngoscope cameras, endoscopes (ENT and upper/lower gastrointestinal), as well as camera systems used for various other types of non-invasive endoscopic surgery. Although the designs of these various medical imaging devices can vary greatly, all such medical imaging devices share some basic design similarities. Generally, a medical imaging device will include a probe portion which is placed within or in contact with a patient. An optical system is placed at the distal end of the probe portion. This optical system may include a miniaturized video camera or simply a lens which is connected to a camera via an optical, e.g., fiber optic, cable running from the distal end of the probe to the proximal end thereof. A light source may also be provided at the distal end of the probe via, e.g., a fiber optic cable running through the probe from the proximal end thereof. The proximal end of the medical imaging device probe is connected to a mechanical structure, e.g., a handle, for positioning the probe. Electrical or optical signals from the optical system mounted in the distal end of the probe are provided via an electrical or optical cable to a computer based imaging and/or analysis system. The electrical or optical signals are converted into a video image, which may be displayed to a user of the device, and other observers, on a system monitor or display. The video image may also be digitized and operated upon by the computer imaging/analysis system for image enhancement and detailed computer analysis of the image.

Since medical imaging devices, and particularly the probe portions thereof, come in direct contact with patients and their bodily fluids, measures must be taken to prevent cross-contamination when such imaging devices are used. Typically, the cost, complexity, and design of most medical imaging devices prevents them from being thoroughly cleaned in a conventional manner between each use. Therefore, protective infection control covers are typically used with such medical imaging devices. Such protective covers typically cover at least the probe portion of the medical imaging device, and may extend to cover other portions of the device as well.

Since medical imaging devices depend on good optical performance for their operation, it is important that any protective cover mounted over the distal end of the imaging device probe be integrated into the optical system mounted therein to assure good image quality and repeatable accurate results. Integration of a protective cover into the optical system used in the medical imaging device requires that the protective cover have a shape and be made of a material which does not interfere with the performance of the medical imaging device. Even a properly designed protective cover can adversely affect system performance if the protective cover is not properly mounted on the imaging device. A protective cover which does not meet the exacting optical specifications (shape and material) for a particular medical imaging device, or is not properly mounted on the device, may lead to a poor visual image, or, in the case of a diagnostic device, an inaccurate result.

Optical pattern detection and identification techniques are widely used in various commercial areas. Such techniques are employed, for example, in bar code systems used for product identification. A UPC bar code is placed on a product. A laser-based bar code reading device is used to detect and identify the bar code and, therefore, the product. A similar identification technique is used for mail sorting, by identifying coded strips on the front of envelopes.

Optical pattern detection and identification techniques are also employed by devices which use video images to measure the dimensions of physical objects, such as molded plastic or machined metal parts. Such video inspection systems are commonly used in metrology laboratories, and are built by a number of companies, including Mitutoyo, Brown & Sharpe, RAM Optical Systems, and others. Objects placed upon the working areas of such systems are viewed with surface illumination, or with background (shadowgraph) illumination to show edge detail.

Optical pattern identification techniques are also used for reading printed pages of material. More complex pattern identification systems exist for recognizing hand-written signatures, retinal patterns, and finger prints.

Known methods for identifying geometric patterns, including text characters, involve first digitizing an image which contains the characters or pattern to be identified. The digitized image is provided to a computer system running a pattern recognition program. Relatively simple pattern recognition programs are used for recognizing basic patterns, including text and simple geometric shapes (lines, circles, squares, etc.), within the digitized image. More complex patterns are recognizable through more complex techniques, such as statistical, structural, or syntactic methods. Even more complex patterns can be recognized through the use of neural networks which can be trained to evaluate patterns and interpolate from them. Examples of optical pattern recognition systems and methods are shown in U.S. Pat. Nos. 4,603,976, 4,809,342, and 5,627,895.

SUMMARY OF THE INVENTION

The present invention provides an automated system and method for determining whether a protective cover meeting required specifications is properly mounted on a medical imaging device. The system and method of the present invention employs the optical and imaging/analysis systems of the medical imaging device itself to determine if a protective cover meeting required specifications is in place on the device, and that the protective cover is properly positioned on the device. Visual indicia are placed on a head of the protective cover in the field of view of the medical imaging device optical system. These indicia are included in the video image formed by the optical system. The video image is digitized and analyzed by the medical imaging device imaging/analysis system using pattern recognition algorithms to detect and identify the indicia. The visual indicia may provide information on the nature of the protective cover, e.g., its size, shape, composition, etc., and may be used as alignment marks for the cover. In accordance with the present invention, the medical imaging device is disabled, or a warning signal is provided, if analysis of the indicia in the video image, or lack thereof, indicates that either a protective cover is not present, an incorrect protective cover is being used, or the protective cover is not properly positioned on the device.

The present invention may be employed to provide for the automatic identification of protective covers for medical, dental or veterinary imaging devices. In such imaging devices a video image is created by a video system having an optical system mounted in the distal end of a probe which is placed within or in contact with a patient to be examined. The video image is digitized and provided to a computer based imaging/analysis system. The computer based imaging/analysis system runs imaging and analysis programs for enhancing, displaying, manipulating, and analyzing the video image data.

In order to prevent cross-contamination, a protective cover is placed over the probe of the imaging device to provide an infection control barrier. The protective cover includes a plastic sheath formed to enclose at least a portion of the probe. A transparent head is secured to the plastic sheath. In accordance with the present invention, a protective cover for a medical imaging device includes visual elements or indicia formed on the head of the cover. The visual indicia are formed on the protective cover in an area of the head thereof which lies in the field of view of the imaging device optical system when the cover is properly positioned on the imaging device probe. The protective cover may be manufactured from any suitable optically transparent material, such as glass or plastics, and may be formed by machining, stamping, thermoforming, casting, molding, or any other process. The visual indicia may be formed as part of the head of the cover through the initial forming process, may be created from a different material added during the forming process, or may be applied after the forming process through printing, etching, plating, painting, or some other process. The visual indicia may be in the form of basic geometric shapes (one or more circles, lines, points, polygons, etc.) or more complex outline shapes, may include one or more characters of text, including letters and numbers and/or may include a series of geometric or text elements presented with specific dimensional intervals. The indicia may be conventional machine readable characters such as bar codes. In any case, the indicia will preferably identify the protective cover by size, type, material, etc. The indicia may also be used as alignment markings and/or to provide system calibration data.

Since the indicia are provided on the protective cover in the field of view of the medical imaging device optical system, the digitized video image provided to the device imaging/analysis system will include the indicia if the cover is properly mounted on the device over the device probe. In accordance with the present invention, the digitized video image is processed by pattern recognition algorithms in programs running on the imaging/analysis system computer to detect and identify indicia appearing in the video image. Edge-detection algorithms may be used to detect the perimeters of indicia based on "brightness" and "darkness" data contained in the video image signal. Contrast enhancement algorithms may be run against the digital image data to enable improved edge detection. The perimeter data is analyzed by pattern recognition algorithms to recognize specific features of the indicia, including lines, curves, or polygons. Recognized indicia patterns are compared with stored indicia patterns to ascertain whether the detected indicia are a valid match for the stored patterns.

If the indicia pattern recognized in the video image does not match any stored valid indicia pattern, the protective cover identification system of the present invention will provide a warning to a user of the imaging device that an incorrect protective cover has been placed on the device. Alternatively, the identification system of the present invention will disable operation of the imaging device unless a valid indicia pattern is recognized. The identification system of the present invention may also provide a warning to a user of the imaging device if the correct indicia pattern does not appear in the proper location on the video image, thereby indicating that the protective cover is not properly positioned on the imaging device. The recognized indicia may also be employed by the imaging device imaging/analysis system for other purposes, such as setting focal distances, calibrating size or distance measurements, or zeroing contrast and brightness settings, depending upon the data provided by the indicia.

The protective cover identification system and method of the present invention may be used in combination with any medical, dental, or veterinary imaging or diagnostic device. The present invention provides an automated system and method for assuring that a protective cover is in place on the imaging or diagnostic device, that the correct protective cover is being used, and that the protective cover is positioned and oriented correctly. Thus, the present invention provides an automated system and method for both ensuring that an infection control barrier is in place and for ensuring that the barrier that is used does not adversely affect operation of the imaging device with which it is employed.

Further objects, features, and advantages of the present invention will be apparent from the following detailed description when taken in conjunction with the accompanying drawings.

DETAILED DESCRIPTION OF THE INVENTION

Figure 1:
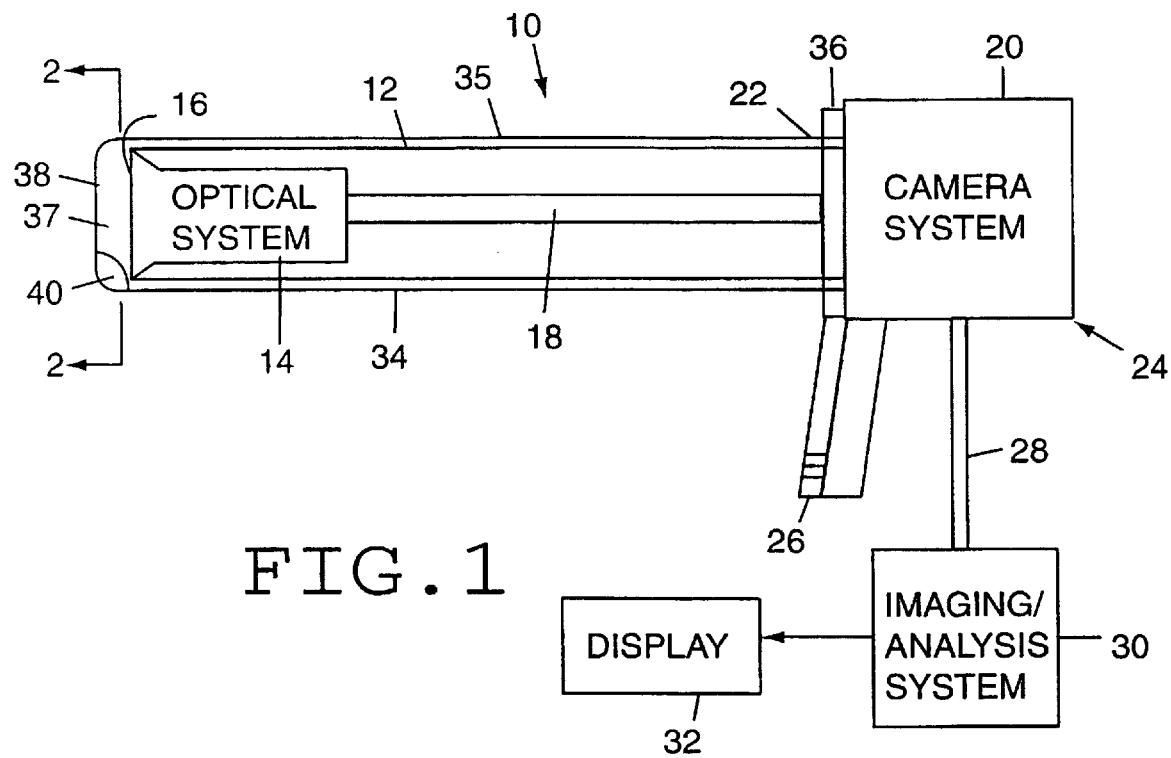
FIG. 1 is a schematic illustration of an exemplary medical, dental or veterinary imaging and diagnostic device employing a protective cover identification system in accordance with the present invention.

The present invention provides an automated system and method for identifying protective covers used on medical imaging devices. The present invention automatically determines that a protective cover is in place, that the correct protective cover is used, and that the protective cover is correctly positioned and oriented on the imaging device. The present invention may be employed in combination with any medical, dental, or veterinary imaging and/or diagnostic device employing optical or video imaging. Such devices include dental cameras, retinal cameras, laryngoscope cameras, endoscopes (ENT and upper/lower gastrointestinal), as well as camera systems used for various other types of non-invasive endoscopic surgery. To emphasize the fact that the present invention is generically applicable to a wide variety of such imaging and diagnostic devices, the present invention will be described with reference to the schematic illustration of a generic medical imaging device 10 of FIG. 1. Although different types of medical imaging and diagnostic devices vary greatly in the details of their design and construction, most such devices will include the basic components included in the exemplary generic medical imaging device 10.

The medical imaging device 10 includes an optical or visual sensing structure, typically in the form of a probe 12 or the like. As used herein, the probe is generally the portion of the medical imaging device that comes in contact with the patient, including non-invasive contact as with the skin and contact by insertion in body cavities and surgical wounds. The probe 12 may be formed, for example, from a rigid, semirigid, or flexible tube. An optical system 14 is mounted at a distal end 16 of the probe 12. The optical system 14 typically includes one or more lenses (not shown) having a field of view directed outward from the distal end 16 of the probe 12. Alternatively, the field of view of the optical system 14 may be at an angle with respect to the axis of the probe 12, and thus may be directed outwardly from the side of the probe 12. The lenses in the optical system 14 mounted in the probe 12 may be connected directly to a miniaturized video camera which is also mounted in the probe 12 and forms part of the optical system 14. Alternatively, an optical image may be carried from the lens in the optical system 14 at the distal end 16 of the probe 12 via, e.g., a fiber optic cable 18, to a video camera system 20 located at the proximal end of the probe 12. If the video camera is included as part of the optical system 14 mounted in the distal end 16 of the probe 12, the cable 18 may include one or more wires for carrying an electrical video signal from the optical system 14 to the proximal end 22 of the probe 12. Depending upon the nature of the imaging device 10, the device probe 12 may include other useful structures (not shown) such as a light source provided at the distal end 16 of the probe via, e.g., a fiber optic cable running through the probe from the proximal end 22 thereof.

The proximal end 22 of the probe 12 is connected to a base unit 24 of the imaging device. Base unit 24 includes a handle 26 or other structure for mounting or supporting the imaging device 10 such that the distal end 16 of the probe 12 can be placed within or in contact with the body of a patient at a desired location and position. The camera system 20 is also mounted in the base unit 24. The camera system 20 converts the optical or electrical signal provided by the optical system 14 mounted in the distal end 16 of the probe 12 into an electrical video signal which is provided on a cable 28 to an imaging/analysis system 30. As described previously, the camera system 20, or a portion thereof, may be mounted within the probe 12 adjacent to or as a part of the optical system 14 mounted in the distal end 16 of the probe 12.

The imaging/analysis system 30 is typically remotely located from the rest of imaging device 10 so as to not interfere with use of the imaging device 10. The imaging/analysis system 30 is connected to the rest of the remotely located imaging device 10 via the connecting cable 28. The video signal provided on the cable 28 to the imaging/analysis system 30 may be analog or digital in nature. If the video signal provided to the imaging/analysis system 30 is analog, the video image signal may be provided directly to a display 32, such as a video monitor, connected to the imaging/analysis system 30. The imaging/analysis system 30 is typically implemented using a general or special purpose computer including conventional personal computers. Preferably, the video image signal is digital in nature, or is converted into a digital signal within the imaging/analysis system 30. The digitized video signal may be operated upon by programs running within the imaging/analysis system 30 to enhance the video image before it is displayed on the video display 32. Programs running in the imaging/analysis system 30 may also be used to manipulate and analyze other information contained in the digitized video image. Such computerized analysis of the digitized video image signal may be used, for example, to automatically locate physical structures of interest within the video image or provide a numerical analysis of information contained within the video image. The results of this computerized analysis of the digitized video image may be displayed on the display 32, either in conjunction with or separate from the video image itself.

In order to prevent cross-contamination between patients, or from patients to medical personnel or vice-versa, it is important to ensure that any portion of the imaging device 10 which comes in contact with or in close proximity to patients and their bodily fluids be thoroughly clean. However, due to the complexity and expense of the imaging device 10, it is often not practical or possible to thoroughly clean the device between each use. Therefore, a protective cover 34 is placed over portions of the imaging system 10 which will come in contact with patients and their bodily fluids to provide an infection control barrier for the device. As illustrated in FIG. 1, the protective cover 34 includes a plastic sheath (which may be flexible, rigid or semi-rigid) that is formed to fit over and enclose at least a portion of the probe 12. A transparent head 37 is secured to the sheath 35 at the distal end 38 of the cover. The sheath 35 of the protective cover 34 may be extended to also cover the base unit 24 of the imaging system 10, or a separate protective cover may be placed over the base unit 24, to provide a more complete infection control barrier. A more complete infection control barrier may be required, for example, where the imaging device 10 is employed in surgical situations. An attachment structure or mechanism 36 may be provided on the base unit 24 for attaching the protective cover 34 over the probe 12 to the base unit 24. The exact nature and design of the attachment mechanism 36 will depend on the design of the imaging device 10 and probe 12 employed on the imaging device 10.

The protective cover 34 may be made of a variety of rigid, semi-rigid, or flexible materials. The protective cover 34 may be made of a material which may be cleaned and reused, or may be made disposable after each use. Exemplary materials from which the protective cover 34 may be manufactured include glass and plastic. The protective cover 34 may be made of different materials along its length. However, the head 37 at the distal end 38 of the protective cover 34, within the field of the view of the optical system 14, provides a transparent window or "lens" (typically, non-focussing) at the distal end of the probe and is made of an optically transparent material. The head 37 may comprise a solid transparent disk. The protective cover 34 may be made in various ways. For example, the cover 34 may be made as a single injected molded part (integrally formed head and sheath) or with an injected head 37 (lens) that is insert molded with an extruded tube as the protective sheath 35 that will extend over the probe 12. The head (lens) portion 37 of the single injection molded part or the injected head (lens) portion 37 of the insert molded part is preferably made from optically clear, potentially sterilizable thermoplastic resins with inherent low birefringence. Two examples of resins that meet these requirements that may be used to make the head (lens) 37 of the cover are polymethylmethacrylate (acrylic or PMMA) and polymethylpentane (PMP). The tooling cavities to mold the lens portion 37 are preferably single-point and diamond-turned, in order to provide excellent optical transparency. An extruded tubular portion which forms the sheath 35 of the insert molded part may be made from a sterilizable plastic resin that may be thermally, ultrasonically or mechanically bonded to the injection molded lens 37 of the cover. Examples of plastic resins which may be used to form the sheath 35 are low density polyethylene and ethylene vinyl acetate. Typically, the sheath 35 is flexible and is formed to fit snugly on the probe. The cover may be formed to conform to the probe as described in U.S. Pat. No. 5,743,849, incorporated herein by reference. The fabrication of protective covers for imaging systems 10 generally, including methods of manufacture and materials from which the covers may be manufactured, are well known to those skilled in the art.

Figure 2:
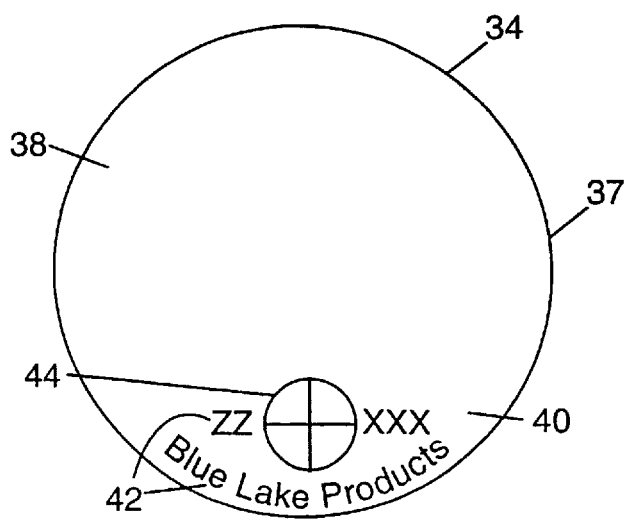
FIG. 2 is a cross-sectional view of an exemplary protective cover employed in a protective cover identification system and method in accordance with the present invention as taken generally along line 2—2 of FIG. 1, showing exemplary visual elements or indicia formed in the head of the cover.

In accordance with the present invention, visual elements or indicia are formed on a portion 40 of the head 37 at the distal end 38 of the protective cover 34 within the field of view of the optical system 14 of the imaging device 10. A view of the head 37 at the distal end 38 of an exemplary protective cover 34 in accordance with the present invention, as viewed from the optical system 14 of an imaging device 10, is presented in FIG. 2. As illustrated, the portion 40 of the head 37 of the protective cover 34 having the visual indicia formed thereon preferably only extends over a small portion of the field of view of the optical system 14. This will minimize any interference by the indicia with objects of interest to be viewed by the imaging system 10. Of course, the portion 40 of the head 37 of the cover 34 having visual indicia formed thereon may be larger or smaller than that illustrated.

The visual elements or indicia may be formed on the head 37 of the protective cover 34 in a variety of ways. For example, the indicia may be formed as part of the head of the protective cover 34 through the initial forming process. Thus, the indicia may be formed as molded-in features (e.g., surface bosses or indentations) of the head of the protective cover 34 which will provide image contrast when light is projected through the head. Alternatively, the visual elements or indicia may be formed during the forming process of the protective cover 34 by use of an additional material added (e.g., on the surface or embedded) during the forming process. The visual elements or indicia may be applied to the head of the cover 34 after the process of forming the cover 34 is complete, such as through printing, etching, plating, or other processes. It is apparent that the visual elements or indicia formed on the head 37 of the protective cover 34 may be formed in any manner.

The visual elements or indicia formed on the protective cover 34 may take a variety of forms. For example, one or more characters of text 42 may be formed on the head of the protective cover 34. The text may indicate the source of the cover, e.g., the manufacturer's trademark, and/or other information about the cover, such as its type, size, etc. The textual elements may also provide information on the material or optical characteristics of the cover 34. The visual elements or indicia may take the form of basic geometric shapes 44, such as one or more circles, lines, points, polygons, etc., or more complex outline shapes. These simple or complex geometric shapes may also be used to indicate the manufacturer, type, size, nature, or composition of the cover 34. The visual elements or indicia may also be formed as a series of geometric or text elements with specific dimensional intervals between the elements, such as a UPC bar-type code or other machine readable characters. In such a case, information on the manufacturer, type, size, or other characteristics of the cover may be found in the text elements or geometric shapes and/or the size or nature of the intervals between the characters or shapes. In accordance with the present invention, the visual elements or indicia formed on the head of the cover 34 may take any form capable of conveying information.

In accordance with the present invention, the visual elements or indicia formed on the head 37 of the cover 34 are formed on a portion 40 thereof which is positioned in the field of view of the optical system 14 of a medical imaging device 10. Thus, the visual elements or indicia formed on the head 37 of the protective cover 34 will appear in the video image produced by the optical and camera systems of the imaging device. Ambient light, or light from a specifically designed source, such as light from a light source mounted in the probe 12 and reflecting off of portions of the patient's body being viewed by the imaging device 10, will shine through the head 37 at the distal end 38 of the protective cover 34 and will be picked up as areas of "brightness" by the imaging device optical system 14. The visual elements or indicia formed on the distal end 38 of the protective cover 34 are designed to block or interfere with light entering the distal end 16 of the probe 12 in the areas wherein they are located. Thus, the areas in the field of view of the optical system 14 wherein the visual elements or indicia are located will show up typically as areas of "darkness" in the image picked up by the optical system 14. The areas of brightness and darkness which are picked up by the optical system 14 form the video image which is provided in digital form to, or converted to a digital form by, the imaging/analysis system 30.

Although the video image may be manually analyzed by the operator, in accordance with the present invention, the digitized video image is preferably automatically analyzed to determine the existence of, position of, and information provided by the visual elements or indicia (generally, patterns) found within the video image which correspond to the visual elements or indicia formed on the head of the protective cover 34. This analysis is performed using algorithms implemented as computer programs running in the imaging/analysis system 30. The visual indicia analysis programs may include edge-detection algorithms which are used to detect the perimeters of the indicia in the video image based on the data in the video signal. Conventional edge-detection algorithms known in the art may be employed to detect the perimeters of the indicia in the video signal. Such edge detection algorithms are described in, e.g., E. Gose, et al., *Pattern Recognition and Image Analysis* (book), CRC Press, 1997; F. Kammoun et al., "Optimum Edge Detection For Object-Background Picture," Graphical Models and Imaging Processing, 1994, pp. 25–28; and M. J. J. Wang, et al., "A New Edge Detection Method Through Template Matching," International Journal of Pattern Recognition and Artificial Intelligence, 1994, pp. 899–917. Such conventional edge-detection processes generally require only that a weighted matrix multiplication be performed against data points in the digitized video image array. To enable improved edge detection, the visual indicia analysis programs may include contrast enhancement algorithms. Contrast enhancement algorithms are particularly useful in cases where the visual elements or indicia are formed as molded-in features of head of the cover 34, created by replication of a dimensional feature, or are engraved or etched into the head 37 of the cover 34, or in other cases wherein the contrast levels of the visual elements or indicia may be relatively low. Such contrast enhancement algorithms are described in, e.g., P. Meer, et al., "Multiresolution Adaptive Image Smoothing," Graphical Models and Image Processing, 1994, pp. 140–148; and T. P. Kaushal, "Visibly Better Edge Detection Using Observed Image Contrasts," Pattern Recognition Letters, 1994, pp. 641–647.

Pattern recognition algorithms are used to recognize and interpret the perimeter data derived by the edge-detection algorithms. Conventional pattern recognition algorithms may be employed for this purpose to "read" the text characters or geometric shapes found in the video image. Such pattern recognition algorithms are described in, e.g., B. Jahne, et al., *Digital Image Processing— Concepts, Algorithms, and Scientific Applications* (book), Springer-Verlag, 1991; J. C. Russ, The Image Processing Handbook, CRC Press, 1995; R. Cole, et al., "On the Detection of Robust Curves," Graphical Models and Image Processing, 1994, pp. 189–204; U. Seeger, et al., "Fast Corner Detection in Gray-Level Images," Pattern Recognition Letters, 1994, pp. 669–675; B. Bhavnagri, "A Method For Representing Shape Based on an Equivalence Relation on Polygrams," Pattern Recognition, 1994, pp. 247–260. Pattern Recognition may also be carried out as described in the foregoing U.S. Pat. Nos. 4,603,976, 4,809,342, and 5,627,895, incorporated by reference. The recognized characters and shapes are compared to visual indicia elements stored in memory which correspond to and indicate protective covers 34 which are known to be appropriate for use with the particular imaging device 10 to provide satisfactory infection control without affecting performance of the device 10. If a match between the visual elements recognized in the video image and valid visual elements stored in memory is not found, the imaging/analysis system of the present invention will determine that an appropriate protective cover is not in place on the imaging device 10.

In accordance with the present invention, the imaging/analysis system 30 may be programmed to take various actions in response to the determination that an appropriate protective cover 34 is not in place on the imaging system 10. If the analysis of the digitized video image results in a determination that no visual elements or indicia are found in the video image, or that the visual elements or indicia found in the video image do not correspond to valid visual elements or indicia stored in memory (preselected patterns), a warning may be provided on the display 32 to a user of the imaging device 10. Additionally, the imaging/analysis system 30 may disable the imaging device 10, to prevent its use, in such a case. The system thus provides an indication of whether the pattern has been found in the image. If the proper pattern is found, rather than being a warming or message, the indication may be absence of a message or may be a command to allow imaging to proceed.

In accordance with the present invention, the imaging/analysis system 30 may also be programmed to determine the location of visual elements or indicia (a preselected pattern) in the digitized video image, and to compare the detected locations with valid locations for the visual elements or indicia stored in memory. If the visual elements or indicia found in the digitized image are not found to be in a valid location, but are otherwise valid indicia, a warning may be provided on the display 32 indicating that the protective cover 34 is not properly positioned on the imaging device 10. The system may also compare the orientation of the pattern found in the image with a valid orientation, and provide an indication of whether the pattern is in the valid orientation. In addition, the imaging/analysis system 30 may disable use of the imaging device 10 if the protective cover 34 is found to be improperly positioned or oriented.

Information contained in the visual elements or indicia recognized in the digitized video image also may be employed by the imaging/analysis system 30 for calibration of the imaging device 10 or other purposes. For example, information contained in the recognized visual indicia concerning the optical characteristics of the protective cover 34 may be used by the imaging/analysis system 30 for setting the focal distance of the imaging device 10, calibrating size or distance measures, or zeroing contrast and brightness settings.

Figure 3:
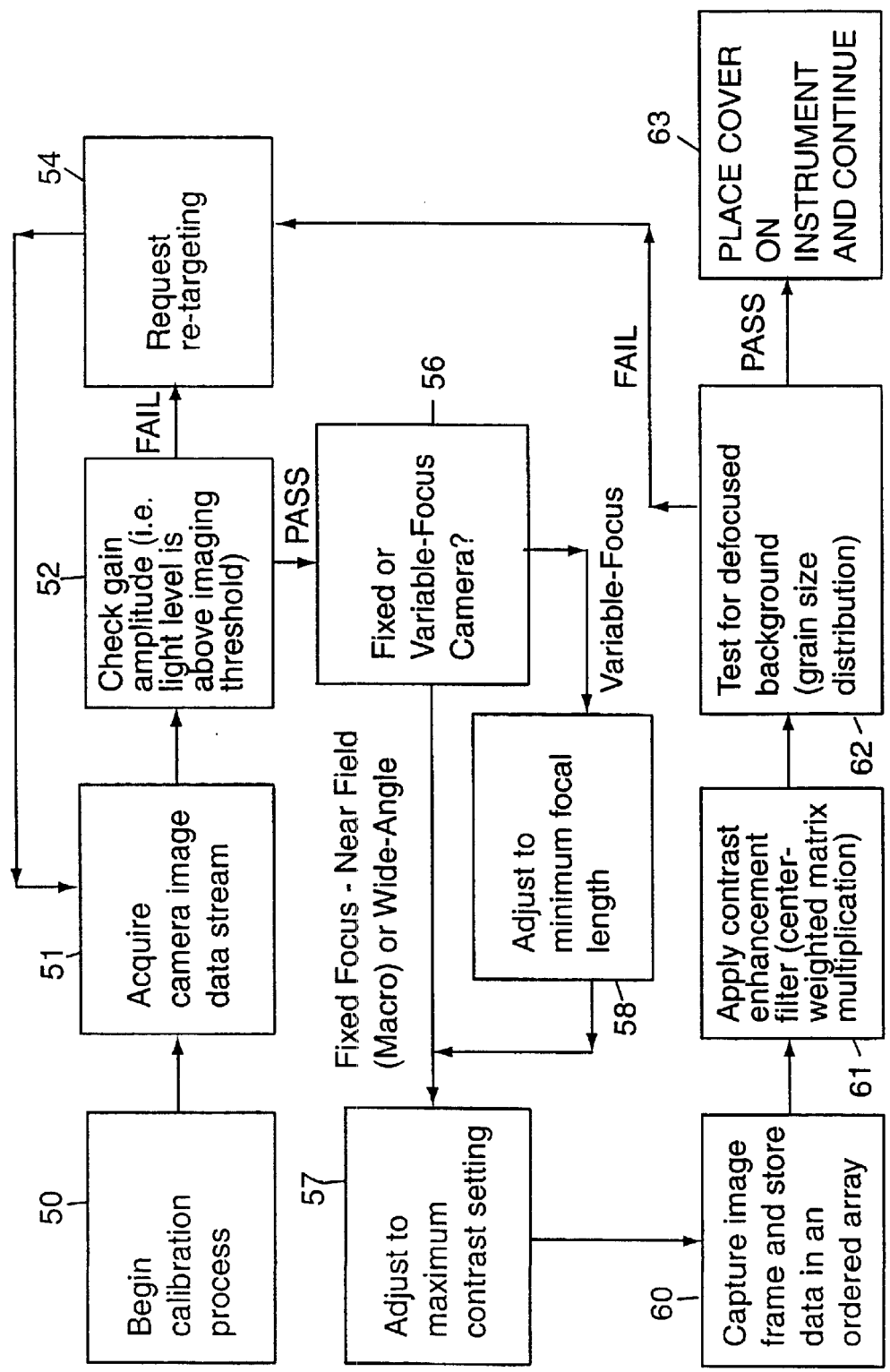
FIG. 3 is a flow chart of a computer implemented calibration process for protective cover recognition in accordance with the invention.

For purposes of exemplification, a flow chart of a calibration process implemented by the computer of the system 10 in accordance with the invention is shown in FIG. 3. This process is carried out prior to the protective cover recognition process and exemplifies the calibration that may be utilized with generally diffused ambient light. A simplified process may be utilized where a standard target light source and positioning fixture are available.

With reference to FIG. 3, the calibration process begins at the command of the operator at 50 and proceeds to acquire a camera image data stream at 51. The gain amplitude of the camera is checked at 52 to determine if the light level is above the imaging threshold. If the check at 52 fails, a request for retargeting is issued at 54, and the system proceeds back to acquire new camera image data at 51. If the gain amplitude is acceptable at 52, a check is made to determine if a fixed or variable focus camera is utilized at 56; if the camera is fixed focus and near field (macro) or wide angle, the program proceeds to adjust to maximum contrast setting at 57; if a variable focus camera is utilized, the program adjusts to the minimum focal length at 58 and then proceeds to adjust to the maximum contrast setting at 57. The program then proceeds at 60 to capture an image frame and store the data in an ordered array and then apply a contrast enhancement filter to the data (e.g., a centered-weight matrix multiplication) at 61. The process then proceeds to test at 62 for defocus background (grain size distribution), which, if passed, results in a message to the operator at 63 on the display device to place the cover on the instrument and continue. If the test at 62 is failed, the program proceeds to block 54 to request retargeting and then continues as described above.

Figure 4:
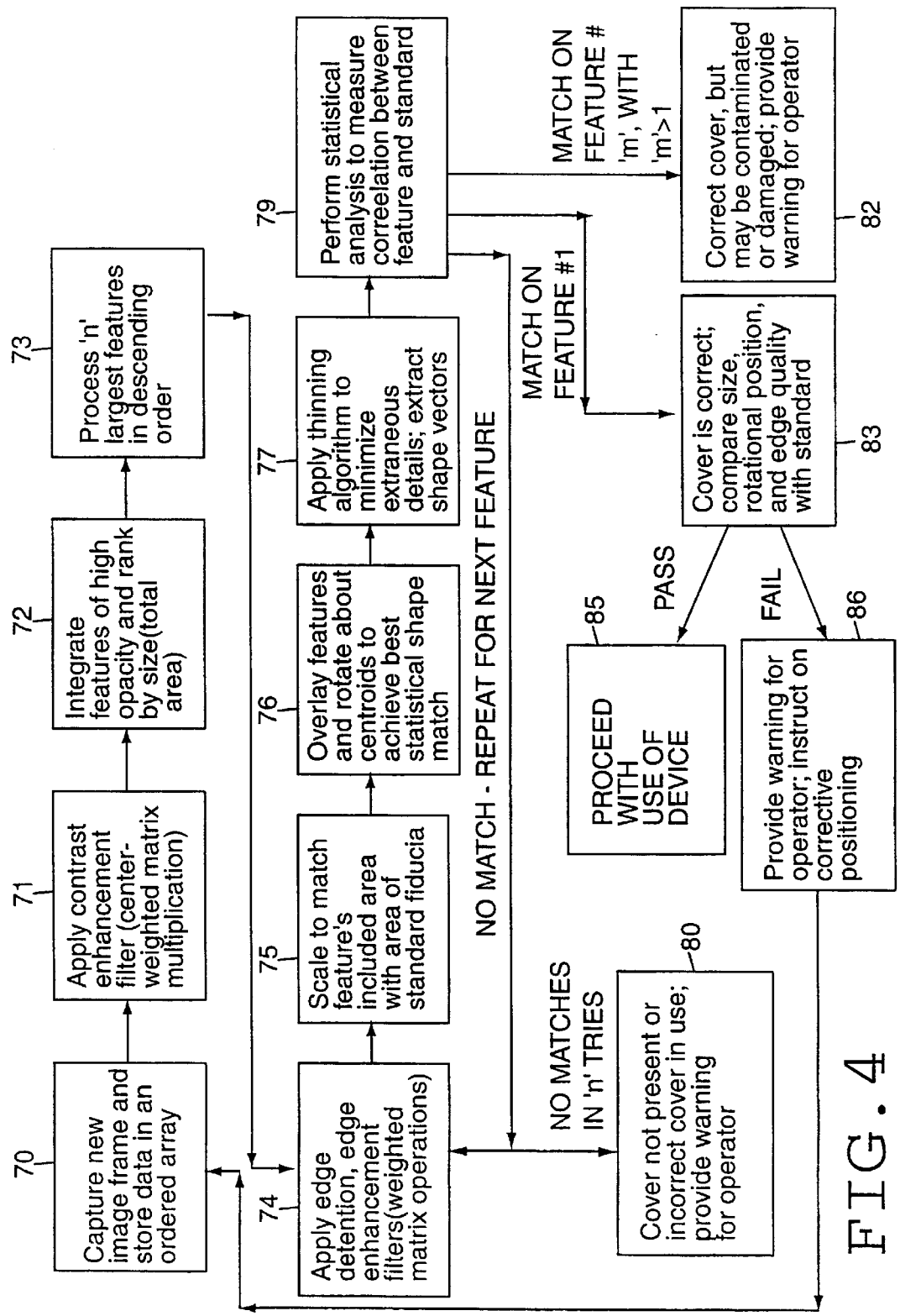
FIG. 4 is a flow chart of a computer implemented protective cover recognition process in accordance with the invention.
Figure 5:
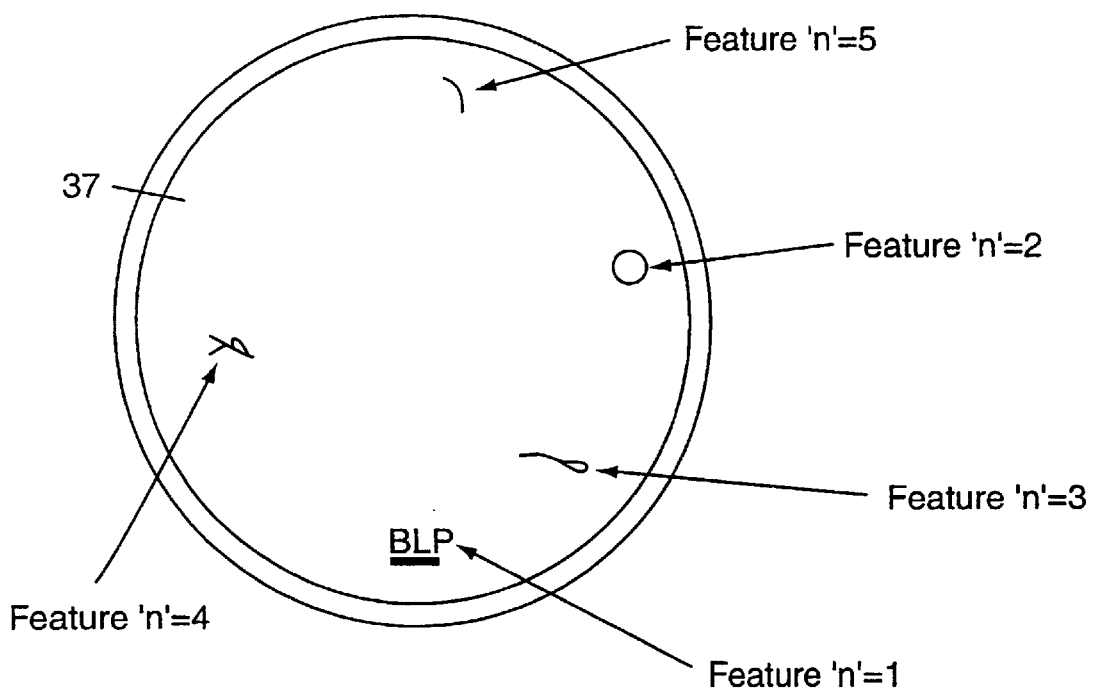
FIG. 5 is a view of the head of an exemplary cover as in FIG. 2 showing examples of features of the head of the cover that may be detected and screened in accordance with the invention.

Once calibration has been completed, the system may then proceed on to the protective cover recognition process, exemplified by the flow chart of FIG. 4, and illustrated with respect to an example of a protective cover shown in FIG. 5 that illustrates various types of features that may be screened for identification significance in accordance with the invention. With reference to the flow chart of FIG. 4, the cover recognition process begins upon command of the operator at 70 to capture a new image frame and store the data in an ordered array. A contrast enhancement filter is then applied at 71, for example, a center-weighted matrix multiplication, and the program proceeds to the block 72 to integrate the features of high opacity and rank by size (total area). The program then proceeds at 73 to process the "n" largest features in descending order where "n" is a preselected number or a number selected by the operator. For example, referring to the illustration of FIG. 5, there are five features of various size on the cover that would be imaged by the camera, each of which is then ranked according to the size or total area occupied by each such feature.

After the processing at 73, the program proceeds to 74 to apply edge detection and edge enhancement filters (weighted matrix operations), and then at 75 proceeds to scale to match the features included with the area of standard fiducial marks. The program then proceeds at 76 to overlay features and to rotate about centroids to achieve the best statistical shape match, and then proceeds at 77 to apply a thinning algorithm to minimize extraneous details and to extract shape vectors. Statistical analysis is performed at 79 to measure the correlation between the feature and the standard. A first possible result of the analysis is that there is no match, in which case the program proceeds back to the block 74 to again apply edge detection, etc. If no matches have been obtained in "n" tries, where "n" is a number preselected or selected by the operator, a message is provided at 80 (e.g., an audible warning or a message on the video screen for the imaging device) that the cover is not present or an incorrect cover is in use, and a warning is issued for the operator. If the analysis at 79 indicates that a match has been obtained but more than one feature has been matched, a warning (indication) is issued at 82 that the cover is correct but may be contaminated or damaged. If the analysis at 79 indicates at match on feature number 1 (the largest feature), the cover is determined to be correct, and the program proceeds at 83 to compare the size, rotational position and edge quality with the standard. If it passes this test, the program proceeds to issue a message at 85 that the test has been passed and the operator should proceed with use of the device; if the test at 83 is failed, the program provides a warning to the operator as indicated at 86 and may instruct the operator on corrective positioning of the cover. If the system determines that a proper cover is being used and is properly positioned, the operator then proceeds to use the imaging device to take an image through the head of the cover of a body structure for examination of the body structure. After the examination has been completed, the operator then removes the cover from the probe and, generally, disposes of the cover. The protective covers of the invention may be formed inexpensively of plastic materials, allowing economic disposal after use, thereby minimizing the likelihood of cross-contamination of patients.

It is understood that this invention is not confined to the particular embodiments herein illustrated and described but embraces all such forms thereof as come within the scope of the following claims.

What is claimed is:

1. A disposable protective cover for a medical imaging device of the type having a probe with an optical system at a distal end of the probe that receives light that is imaged by the medical device, comprising:
   (a) a sheath of plastic material formed to enclose at least a portion of the probe of the medical imaging device; and
   (b) a transparent head secured to the sheath at a distal end of the cover, the transparent head formed to provide a transparent window at the distal end of the probe when the cover is mounted on the probe, the transparent head formed to optically transmit light therethrough to the distal end of the probe, the transparent head having visual indicia thereon in a position that will be within the field of the medical imaging device at its distal end;
   wherein the cover formed by the sheath and transparent head is formed to protect the enclosed portion of the probe from contamination when a medical device with the cover attached thereto is used in a medical procedure.

2. The cover of claim 1 wherein the indicia are selected from the group consisting of geometric patterns, letters, numbers, and combinations thereof.

3. The cover of claim 1 wherein the indicia include machine readable markings.

4. The cover of claim 3 wherein the machine readable markings are bar code characters.

5. The cover of claim 1 wherein the transparent head is formed of plastic.

6. The cover of claim 5 wherein the sheath and head are integrally formed together of the same plastic.

7. The cover of claim 5 wherein the head is formed as a transparent circular disk of plastic.

8. The cover of claim 5 wherein the indicia are molded into the plastic forming the transparent head.

9. The cover of claim 5 wherein the indicia are printed on the surface of the transparent head.

10. The cover of claim 5 wherein the head is formed of a disk of solid transparent plastic and the sheath is formed of a flexible plastic joined thereto.

11. Medical imaging apparatus comprising:
    (a) a medical imaging device having a probe with an optical system at a distal end of the probe which receives light at the distal end and provides image data corresponding to the image of the light received at the distal end of the probe;
    (b) a cover extending over at least a portion of the probe comprising a sheath of plastic material formed to enclose at least a portion of the probe of the medical imaging device, and a transparent head secured to the sheath at a distal end of the cover, the transparent head formed to provide a transparent window at the distal end of the probe, the transparent head formed to optically transmit light therethrough to the distal end of the probe, the transparent head having visual indicia thereon in a position within the field of the medical imaging device at its distal end; and
    (c) processing means receiving the image data from the medical imaging device for analyzing the image data and recognizing selected indicia in the image from the medical imaging device corresponding to indicia on the head of the probe.

12. The medical imaging apparatus of claim 11 wherein the medical imaging device is an endoscope.

13. The medical imaging apparatus of claim 11 wherein the indicia are selected from the group consisting of geometric patterns, letters, numbers, and combinations thereof.

14. The medical imaging apparatus of claim 11 wherein the indicia include machine readable markings.

15. The medical imaging apparatus of claim 14 wherein the machine readable markings are bar code characters.

16. The medical imaging apparatus of claim 11 wherein the transparent head is formed of plastic.

17. The medical imaging apparatus of claim 16 wherein the sheath and head are integrally formed together of the same plastic.

18. The medical imaging apparatus of claim 16 wherein the head is formed as a transparent circular disk of plastic.

19. The medical imaging apparatus of claim 16 wherein the indicia are molded into the plastic forming the transparent head.

20. The medical imaging apparatus of claim 16 wherein the indicia are printed on the surface of the transparent head.

21. The medical imaging apparatus of claim 16 wherein the head is formed of a disk of solid transparent plastic and the sheath is formed of a flexible plastic joined thereto.

22. A method of covering a medical imaging device to protect against the spread of infection, the medical imaging device of the type having a probe with an optical system at a distal end of the probe which receives light at the distal end to provide data corresponding to an image of the light received at the distal end, comprising:

(a) applying a cover over the probe of the medical imaging device, the cover comprising a sheath of plastic material formed to enclose at least a portion of the probe of the medical imaging device, and a transparent head secured to the sheath at a distal end of the cover, the transparent head formed to provide a transparent window at the distal end of the probe when the cover is mounted on the probe, the transparent head formed to optically transmit light therethrough to the distal end of the probe, the transparent head having visual indicia thereon in a position within the field of the medical imaging device at its distal end;

(b) taking an image with the medical imaging device of the head of the cover to provide image data;

(c) analyzing the image data to determine if the image data includes a preselected pattern; and (d) providing an indication of whether the pattern has been found in the image.

23. The method of claim 22 further including, before the step of applying a cover over the medical imaging device, the step of taking a calibration image with the medical imaging device to provide calibration image data, and wherein in the step of analyzing the image data corresponding to the image of the head of the cover, utilizing the calibration image data to calibrate the image data from the image of the head of the cover.

24. The method of claim 22 further including disabling the operation of the medical imaging device if the preselected pattern is not found in the image data corresponding to the image of the head of the cover.

25. The method of claim 22 further including taking an image with the medical imaging device through the head of the cover of a body structure for examination of the body structure, then removing the cover from the imaging device and disposing of the cover.

26. The method of claim 22 wherein the preselected pattern is selected from the group of patterns consisting of geometric patterns, numbers, letters, machine readable graphics, and combinations thereof.

27. The method of claim 26 wherein the preselected pattern is an indicator of information concerning characteristics of the cover, and including the further steps if the preselected pattern is recognized of providing a message to an operator indicating the characteristics of the cover that correspond to the preselected pattern.

28. The method of claim 22 wherein if the preselected pattern is found, determining the location of the pattern and comparing the location to a valid location, and providing an indication of whether the pattern is in the valid location.

29. The method of claim 22 wherein if the preselected pattern is found, determining the orientation of the pattern and comparing the orientation to a valid orientation, and providing an indication of whether the pattern is in the valid orientation.

30. The method of claim 22 further including analyzing the image data to determine if the image data includes more than one match to the preselected pattern and providing an indication if more than one match is found.

\* \* \* \* \*